United States Patent [19]

Sabahi et al.

[11] Patent Number: 5,430,177

[45] Date of Patent: Jul. 4, 1995

[54] POLYFUNCTIONAL MICHAEL ADDITION PRODUCTS

[75] Inventors: Mahmood Sabahi, Baton Rouge, La.; Matthew L. Hurst, Lafayette, Ind.

[73] Assignee: Albemarle Corporation, Richmond, Va.

[21] Appl. No.: 169,286

[22] Filed: Dec. 20, 1993

Related U.S. Application Data

[60] Division of Ser. No. 947,629, Sep. 21, 1992, abandoned, which is a continuation-in-part of Ser. No. 812,398, Dec. 23, 1991, abandoned.

[51] Int. Cl.$^6$ .............................................. C07C 69/34
[52] U.S. Cl. .................................................... 560/190
[58] Field of Search ................. 560/190, 202; 562/480

[56] References Cited

U.S. PATENT DOCUMENTS 2,396,626  3/1946  Wiest et al. ......................... 260/464
4,795,787  1/1989  Walz .................................. 525/328.2

FOREIGN PATENT DOCUMENTS 238578  8/1990  Japan .

OTHER PUBLICATIONS

Skarzewski, "The Michael Reaction of Methanetricarboxylic Esters. A Simple Method for Two-Carbon Chain Elongation," *Synthesis*, Dec. 1990, pp. 1125–1127.
Search Report-CA83(4):30324q (Lorenz et al., DE 2342539 (03/75).
Derwent Database-85-143099 (Denki Kagaku Kogyo, JP 60-076504 (05/85).

*Primary Examiner*—José G. Dees
*Assistant Examiner*—Samuel Barts
*Attorney, Agent, or Firm*—Philip M. Pippenger; Patricia J. Hogan

[57] ABSTRACT

Compounds varying from liquids to solids can be prepared via a Michael reaction so that they correspond to the formula $DA_m$ in which D is a deprotonated residue of a Michael donor, A is a monovalent group composed of n Michael acceptor moieties, m is an integer of at least one corresponding to the valence of D, and n is an integer of at least one such that the sum of n moieties in the m monovalent A groups is at least three. Among the more preferred products are the ester oils in which the esterifying groups contain 1–30 carbons and which have viscosities such as to make them suitable for use as lubricants.

5 Claims, No Drawings

POLYFUNCTIONAL MICHAEL ADDITION PRODUCTS

CROSS-REFERENCE TO RELATED APPLICATION

This application is a division of application Ser. No. 07/947,629, filed Sep. 21, 1992, abandoned, which is a continuation in part of application Ser. No. 07/812,398, filed Dec. 23, 1991, abandoned.

FIELD OF INVENTION

The invention relates to Michael addition products. More particularly, it relates to such products containing at least three moieties derived from the Michael acceptor.

BACKGROUND

The Michael reaction is a known process wherein a Michael acceptor (such as an $\alpha,\beta$-ethylenically-unsaturated aldehyde, ester, nitrile, ketone, sulfone, or sulfoxide) is reacted with a Michael donor (such as a dialkyl malonate) to elongate a carbon chain. U.S. Pat. No. 2,396,626 (Wiest et al.) teaches that useful products can be obtained by reacting two molecules of acrylonitrile, an alkyl acrylate, or an acrylamide with a molecule of a donor, such as an ester, amide, or nitrile of malonic acid, phenylacetic acid, cyanoacetic acid, or acetoacetic acid. However, as indicated in Skarzewski, "The Michael Reaction of Methanetricarboxylic Esters. A Simple Method for Two-Carbon Chain Elongation," *synthesis*, December 1990, pp. 1125–1127, it has usually been considered undesirable to add a donor molecule to more than one acceptor molecule in such a reaction.

SUMMARY OF THE INVENTION

The invention resides in (1) novel compounds corresponding to the formula $DA_m$ in which D is a deprotonated residue of a Michael donor, A is a monovalent group composed of n Michael acceptor moieties, m is an integer of at least one corresponding to the valence of D, and n is an integer of at least one such that the sum of n moieties in the m monovalent A groups is at least three and (2) processes for preparing them.

DETAILED DESCRIPTION

The compounds of the invention are polyfunctional compounds which have a structure such that they are most conveniently prepared by reacting one or more Michael donors with one or more Michael acceptors to form a product containing at least three acceptor moieties per donor moiety.

Michael donors which can be used in the reaction include all organic compounds capable of functioning as Michael donors by virtue of containing at least one active hydrogen and at least one electron withdrawing group, although the donors which are sufficiently reactive to permit a reasonably fast reaction are apt to be preferred. Such compounds include, for example, those in which the only active hydrogens and electron withdrawing groups are attached to a single carbon (e.g., malononitrile), those in which active hydrogens and/or electron withdrawing groups are attached to different carbons in an aliphatic or cycloaliphatic chain (e.g., dimethyl succinate, 1,3-cyclohexanedione, and dimethyl 1,4-cyclohexanedicarboxylate), and those in which active hydrogens and/or electron withdrawing groups are present in other electron withdrawing groups (e.g., methyl acetoacetate and di(chloroethyl) malonate). Moreover, when they contain more than one electron withdrawing group, those groups may be the same or different and may be any such groups which permit the Michael reaction to occur.

There is no maximum to the number of electron withdrawing groups that may be present in a Michael donor which is used in the practice of the invention; but the donors usually contain 1–4 electron withdrawing groups, and those electron withdrawing groups are most commonly groups such as —CN, —COOR, —C(O)R', —OAr, —OR, —NR$_2$, —SO$_2$R, —SO$_2$Ar, —S(O)R', —SR, —CF$_3$, —F, —Cl, —Br, and —I, in which Ar is an aryl group and R and R' generally represent aliphatic, cycloaliphatic, or alphyl groups of up to 30 carbons, although R' may represent hydrogen.

As already indicated, the aliphatic, cycloaliphatic, and alphyl groups represented by R and R' may be substituted hydrocarbyl groups (e.g., halo—, cyano—, or dialkylamino-substituted alkyl, cycloalkyl, or aralkyl groups). However, except when it is desired to have an electron withdrawing group within an electron withdrawing group to present additional sites for the addition of acceptor moieties, it is usually preferred for the R and R' aliphatic, cycloaliphatic, and alphyl groups to be groups which are at least predominantly hydrocarbyl in nature, i.e., (1) contain only carbon and hydrogen or (2) contain carbon, hydrogen, and one or more other atoms but contain so few of the other atoms that the predominantly hydrocarbyl nature of the group is preserved.

When a predominantly hydrocarbyl R or R' group (or any other predominantly hydrocarbyl group mentioned hereinafter) contains atoms other than carbon and hydrogen, these other atoms may be part of a chain or ring as hetero atoms, such as oxygen, sulfur, or phosphorus atoms; or they may be present in substituent groups, such as alkoxy, halo, or cyano groups. However, to preserve the predominantly hydrocarbyl nature of the group, the number of hetero atoms or non-hydrocarbyl substituents therein should not exceed 0.3 per carbon and is preferably not more than 0.1 per carbon. These predominantly hydrocarbyl groups can be regarded as being virtually the same as the alkyl, cycloalkyl, aralkyl, and alkenyl groups to which they most closely correspond, so terms such as alkyl, cycloalkyl, aralkyl, and alkenyl, as used hereinafter, should be understood as including the predominantly hydrocarbyl groups as well as the hydrocarbyl groups normally denoted by those terms (except, of course, when the terms are qualified in such a way as to make it clear that they could not refer to the predominantly hydrocarbyl groups—as when the groups contain too few carbons to permit the inclusion of any hetero atoms while fulfilling the requirement of containing $\leq 0.3$ such atoms per carbon.)

Utilizable Michael donors include compounds such as N,N-dimethylaminoethane, N,N'-dimethyldiaminomethane, N,N,N',N'-tetraethyldiaminomethane, diethylsulfone, dipropylsulfone, ethyl phenyl sulfone, dimethylsulfoxide, difluoromethane, dichloromethane, 1,1-dibromoethane, 1,1-diiodopropane, 1,1,1-trifluoroethane, diphenoxymethane, diethoxymethane, methyl vinyl ketone, ethyl vinyl ketone, propyl vinyl ketone, 1,3-cyclohexanedione, 1,4-dicyclohexanedione, 1-methoxypropanethiol, diethylthiomethane, didodecyl malonate, dibenzyl malonate, octadecyl propionate, methyl p-fluorophenoxyacetate, ethyl p-chlorophenylacetate, and methoxypropyl acetate. However, the more preferred donors are those in which the electron withdrawing groups are —COOR, —C(O)R', and/or —CN groups wherein R and R' are alkyl or cycloalkyl groups of up to 10 carbons, most preferably methyl or ethyl.

Exemplary of these more preferred donors are (1) the methyl, ethyl, propyl, isopropyl, butyl, isobutyl, t-butyl, pentyl, hexyl, chlorohexyl, heptyl, octyl, decyl, bromodecyl, ethoxyoctyl, cyclopropyl, cyclopentyl, cyclohexyl, and cyclooctyl esters of (cyclo)alkanoic and substituted (cyclo)alkanoic acids such as acetic, chloroacetic, cyanoacetic, propionic, butyric, bromobutyric, cyclobutanecarboxylic, cyclohexanecarboxylic, and cycloheptane carboxylic acids, (2) the corresponding diesters of 1,1-dicarboxy(cyclo)alkanes and other dicarboxy(cyclo)alkanes (e.g., succinic, glutaric, and higher acids of the oxalic acid series, and 1,4-cyclohexanedicarboxylic acid) in which the (cyclo)alkane moiety is a divalent hydrocarbylene radical derived from a (cyclo)alkane such as methane, ethane, propane, isopropane, butane, isobutane, t-butane, pentane, hexane, heptane, octane, propoxypentane, butoxypentane, nonane, decane, ethoxyoctane, undecane, cyclopentane, cyclohexane, cycloheptane, or cyclooctane; (3) the corresponding diesters of 1,1-dicarboxy-1-cycloalkylmethanes in which the cycloalkyl substituent is cyclopropyl, cyclopentyl, cyclohexyl, or cyclooctyl; (4) the corresponding dicyano- and diacyl-substituted (cyclo)alkanes and cycloalkylmethanes in which the acyl groups are acetyl, propionyl, butyryl, or isobutyryl; and (5) the corresponding cyano-or acyl-substituted (cyclo)alkanoic and cycloalkylethanoic acid esters.

In a preferred embodiment of the invention, the Michael donors employed in preparing the novel products are Z'—CH(E)(E'') compounds wherein Z' is hydrogen or an alkyl or cycloalkyl group of up to 10 carbons, E'' is hydrogen or an electron withdrawing group, and E is an electron withdrawing group—the electron withdrawing group or groups being any of those mentioned above but preferably being —COOR, —C(O)R', and/or —CN groups in which R and R' are alkyl or cycloalkyl groups of up to 10 carbons, preferably methyl or ethyl. The most preferred Michael donors are the dimethyl and diethyl malonates; the methyl and ethyl cyanoacetates, chloroacetates, acetoacetates, and propionylacetates; malononitrile; acetonitrile; acetylacetone; and dipropionylmethane.

Michael acceptors which can be reacted with these Michael donors include all organic compounds capable of functioning as Michael acceptors by virtue of containing at least one double bond activated by at least one electron withdrawing group, although the more reactive acceptors are apt to be preferred. Like the Michael donors, the Michael acceptors may have the one or more electron withdrawing groups attached to aliphatic or cycloaliphatic carbons, may contain electron withdrawing groups within electron withdrawing groups, and most commonly contain electron withdrawing groups selected from —CN, —COOR, —C(O)R', —OAr, —OR, —NR$_2$, —SO$_2$R, —SO$_2$Ar, —S(O)R', —SR, —CF$_3$, —F, —Cl, —Br, and —I, in which Ar, R, and R' have the definitions given above. Moreover, the unsaturated aliphatic and cycloaliphatic compounds bearing these electron withdrawing groups may be otherwise hydrocarbyl, predominantly hydrocarbyl, or non-hydrocarbyl in nature.

Utilizable Michael acceptors include compounds such as methyl vinyl sulfone, vinyl o-tolyl sulfone, p-tolyl styryl sulfone, the vinyl and vinylidene halides, methyl vinyl ether, ethyl vinyl ether, phenyl vinyl ether, methyl vinyl sulfide, ethyl vinyl sulfide, and 1-cyanocyclohexene. However, the more preferred acceptors are compounds such as (1) the methyl, ethyl, propyl, isopropyl, butyl, isobutyl, t-butyl, pentyl, hexyl, chlorohexyl, heptyl, octyl, decyl, bromodecyl, ethoxyoctyl, ethylthiononyl, dodecyl, cyanododecyl, tetradecyl, hexadecyl, octadecyl, eicosyl, cyclopropyl, cyclopentyl, cyclohexyl, and cyclooctyl esters of acrylic, methacrylic, ethacrylic, crotonic, and cinnamic adds, (2) the corresponding esters of 1-carboxy-1-cyanoethylene and corresponding diesters of 1,1-dicarboxy-2-cyanoethylene and 1,1-dicarboxyethylene, (3) nitriles such as acrylonitrile, methacrylonitrile, ethacrylonitrile, dicyanoethylene, and tricyanoethylene, (4) aldehydes such as acrolein, methacrolein, ethacrolein, crotonaldehyde, and cinnamaldehyde, and (5) ketones such as methyl vinyl ketone and ethyl vinyl ketone.

In the preferred embodiment of the invention utilizing Z'—CH(E)(E'') compounds as Michael donors, the preferred Michael acceptors are ordinarily CTT'=CT''G compounds in which T, T', and T'' are independently selected from hydrogen; G', and organic groups (e.g., alkyl, alkoxyalkyl, alkylthioalkyl, cycloalkyl, dialkylaminocycloalkyl, aryl, haloaryl, alkoxyaryl, aralkyl, and alkaryl groups) of up to 20 carbons; and G and G' are electron withdrawing groups —the electron withdrawing group or groups being any of those mentioned above but preferably being —COOR, —C(O)R', and/or —CN groups in which R and R' are alkyl or cycloalkyl groups of up to 20 carbons.

Of these preferred compounds, the Michael acceptors which are apt to be most preferred are (A) those in which T, T', and T'' are hydrogen and G is a—CN, —COOR, or —C(O)R' group wherein R and R' are methyl or ethyl and (B) the corresponding compounds in which one or two of the hydrogens represented by T, T', and T'' is replaced with a G' electron withdrawing group which may be the same as G or a different group selected from —CN, —COOR, and C(O)R'.

The especially preferred Michael acceptors are the methyl and ethyl acrylates, acrylonitrile, dicyanoethylene, tricyanoethylene, methyl vinyl ketone, and ethyl vinyl ketone.

The reaction between the Michael donor and Michael acceptor is conducted in the presence of a basic compound and a phase transfer catalyst at a suitable temperature, usually a temperature of about 0°–150° C., preferably about 20–80° C., and most preferably about 40°–60° C.

The basic compound, which serves to initiate the reaction, may be any other suitable base; but it is preferably an alkali or alkaline earth metal hydroxide, alkoxide, amide, or carbonate, more preferably a sodium or potassium hydroxide, alkoxide, amide, or carbonate, and most preferably potassium carbonate. Although it may be used in any amount sufficient to initiate the reaction, its concentration is usually about 1–50%, preferably 3–30%, and most preferably 5–10%, based on the weight of the Michael donor.

The phase transfer catalyst employed in the process may be any such catalyst having sufficient catalytic activity to permit the addition of the desired number of Michael acceptor molecules to the Michael donor at a desired rate. Such catalysts include common phase transfer catalysts such as aluminum oxide, potassium fluoride, and mixtures thereof. However, the preferred catalysts are ordinarily alkylammonium salts such as tetraalkylammonium chlorides, bromides, fluorides, iodides, sulfates, hydrogen sulfates, carbonates, and phosphates in which the alkyl groups contain 1-20 carbons—salts which are frequently used as phase transfer catalysts. The phase transfer catalyst is used in a catalytic amount, typically an amount such as to provide about 0.1-1 mol of catalyst per mol of Michael donor.

Although the Michael reaction of the invention is usually conducted in the absence of a solvent, it may sometimes be desirable to increase the efficiency of the phase transfer reaction by utilizing a solvent. The solvent, when used, should be a non-nucleophilic substance, e.g., a hydrocarbon, which will maintain the reactants in solution during the reaction but permit easy separation of the products from the reaction mixture. Such solvents include, e.g., toluene, xylene, other alkylbenzenes, hexane, and other saturated hydrocarbons.

The reaction is effected by combining the reactants, initiator, and catalyst, optionally in the presence of a solvent, and maintaining contact between the reactants at the selected reaction temperature until the desired degree of reaction has been effected. It is usually preferred to make the Michael acceptor the last of the ingredients to be charged to the reaction vessel in order to achieve better control of the reaction temperature and hence improved direction of the reaction to the formation of a desired product.

In the Michael reaction of the invention, the type of product formed is determined largely by the acceptor/donor ratio in the reaction mixture—higher ratios leading to the formation of products containing more acceptor moieties per molecule and thus having higher molecular weights. Since the reaction normally leads to the formation of a mixture of products containing different numbers of acceptor moieties per molecule, it permits the production of some molecules containing more acceptor moieties than the number that would theoretically be provided by the amount of acceptor employed in the reaction mixture. However, it is necessary for the reaction mixture to contain at least the stoichiometric requirement of the acceptor, and preferably a stoichiometric excess, in order for the product to contain a substantial amount of a desired product molecule. Thus, e.g., when a product containing three acceptor moieties is desired, the reaction mixture should contain at least the stoichiometrically required three mols of acceptor/mol of donor and preferably contains >3 mols of acceptor/mol of donor; and, when a product containing eight acceptor moieties is desired, it is important for the reaction mixture to contain at least eight mols of acceptor/mol of donor.

Since it is usually preferred for the product molecules to contain about 3-30 acceptor moieties/donor moiety, the acceptor/donor mol ratio in the reaction mixture is most commonly about 3-35/1.

Of the novel $DA_m$ compounds of the invention, those which are preferred are the compounds corresponding to the formula $Z—C(E)(E')_p—Q_s$ in which Z is alkyl, cycloalkyl, or —(CTT'—CT''G)$_w$—CTT'—CHT''G; Q is —(CTT'—CT''G)$_t$—CTT—CHT''G; E' is an electron withdrawing group; T, T', T'', E and G have the definitions given above; p is zero or one; s is respectively two or one; and each of t and w represents zero or a positive integer such that the compound contains at least three, preferably 3-30 G groups.

The most preferred of the $Z—C(E)(E')_p—Q_s$, compounds are (A) those in which p and s are one; Z is —(CTT'—CT''G)$_w$—CTT'—CHT''G; E, E', G, and G' are independently selected from —CN, —COOR, and —C(O)R' groups wherein R and R' represent aliphatic, cycloaliphatic, or alphyl groups containing up to 30 carbons, usually alkyl or cycloalkyl groups containing up to 10 carbons; and the sum of t and w is 1-30, preferably 1-10, and (B) those in which s is two; Z is —(CTT'—CT''G)$_w$—CTT'—CHT''G; E, G, and G' are independently selected from —CN, —COOR, and —C(O)R' groups wherein R and R' represent aliphatic, cycloaliphatic, or alphyl groups containing up to 30 carbons, usually alkyl or cycloalkyl groups containing up to 10 carbons; and the sum of t and w is 0-30, preferably 1-10.

Such compounds are prepared from the aforementioned Z'—CH(E)(E'') donors and CTT'═CT''G acceptors as illustrated in the following equations:

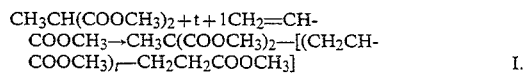    I.

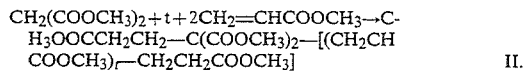    II.

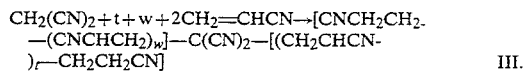    III.

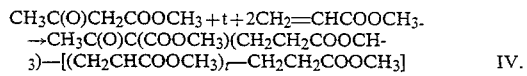    IV.

These reactions are able to proceed until the desired number of acceptor moieties have been combined with the donor, even when the donor contains only one active hydrogen, because the hydrogen donated to an acceptor moiety when the donor is deprotonated becomes an active hydrogen in the acceptor moiety and can be donated to a second moiety where it becomes a donatable hydrogen again. Thus, a reaction such as that summarized in Equation I above would proceed as follows:

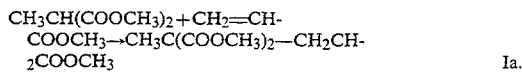    Ia.

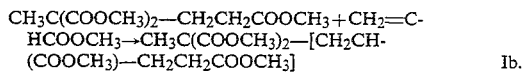    Ib.

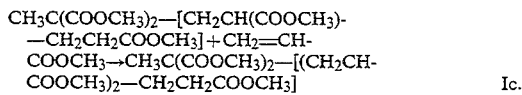    Ic.

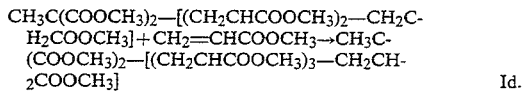    Id.

and continue in the presence of a sufficient amount of acceptor.

As indicated by Equations II and III above, the incorporation of several acceptor moieties into the product molecules is facilitated by utilizing the more reactive $CH_2(E)(E'')$ donors, especially when a $CH_2$═CHG acceptor is employed; and the incorporation of multiple acceptor moieties is also aided by the use of (1) reactants containing the stronger electron withdrawing groups, (2) the higher reaction temperatures, (3) the stronger catalysts, and/or (4) the larger amounts of catalyst. Variations in product structure and properties can be achieved by using mixtures of donor compounds and/or mixtures of acceptor compounds in the reaction.

The products of the Michael reaction may be liquids or solids, depending on the particular reactants and reactant ratios used; and, as already indicated, they are typically mixtures of compounds containing different numbers of acceptor moieties per molecule. If desired, the compounds of the invention, i.e., those containing at least three acceptor moieties per molecule, may be separated from one another and/or from the lower molecular weight Michael products prior to being used in their end application or prior to being subjected to additional reactions preparatory to such use. However, the product mixtures themselves—especially those in which at least about 25% of the product molecules contain at least three acceptor moieties—are also useful materials, so such separations are frequently unnecessary and, in fact, sometimes undesirable. Having a product characterized by a wide molecular weight distribution can be an advantage in providing a balance of properties, as is the case with oils which are to be used in an application wherein some relatively high molecular weight portion is desired to give a required viscosity, but some relatively low molecular weight portion is desired to impart compatibility with a material with which the oil is to be used.

Achieving either a better balance of properties or properties which differ in some other respect from those of the Michael reaction product can also be accomplished by subjecting the product mixture or one or more of the components thereof to one or more of the reactions known to be capable of converting functional groups (i.e., E, E', G, and/or G' groups) in the compounds to different groups. Such reactions, such as the conversion of lower ester groups to higher ester groups, can be conducted by conventional techniques, such as those indexed and outlined in Harrison and Harrison, *Compendium of Organic Synthetic Methods*, Wiley-Interscience (New York), 1971, the teachings of which are incorporated herein by reference.

In addition to having the aforementioned advantage, the post-treatment of the Michael reaction product to prepare a different compound or product mixture of the invention has the benefit of facilitating the preparation of products which it would be at least more difficult to prepare directly by the Michael reaction. For example, it can be beneficial to use a post-Michael reaction conversion of the functional groups when the desired end product is to contain functional groups which, if present in the Michael reactants, would make the Michael reaction relatively slow. Thus, it is apt to be preferred, for example, to react dimethyl malonate with methyl acrylate to provide a first product of the invention and then transesterify that product with hexanol to provide a second product in which the functional groups are hexyl ester groups than to prepare a Michael reaction product from the slower-reacting dihexyl malonate and hexyl acrylate.

Since the Michael reaction and the post-Michael reaction treatments of the Michael products can be tailored to form products which are liquids or solids having widely different molecular weights, the different products of the invention are useful in a variety of applications—the lower molecular weight products being generally most suitable as plasticizers and solvents, the oils usually serving best as lubricants, and the higher molecular weight solids ordinarily being most suited as plastics.

The $DA_m$ oils, especially the $Z-C(E)(E')_p-Q_s$ oils, and most especially the ester oils, constitute a preferred embodiment of the invention. These oils, in addition to having general utility as lubricants, have particular value as refrigeration lubricants, since (1) they can be adapted to have viscosities suitable for refrigeration lubricants (usually 1–600, preferably 5–300, and most preferably 10–200 $mm^2.s^{-1}$ at 40° C.), and (2) their high polarity, together with extensive branching and molecular weight tailoring, can make them completely miscible with common refrigerants, .e.g., ammonia; alcohols such as methanol and ethanol; glycols such as ethylene and propylene glycols; hydrocarbons such as methane, ethane, propane (R-290), butane, ethylene, and propylene; and halocarbons and/or halohydrocarbons such as chlorotrifluoromethane, dichlorodifluoromethane, dichlorofluoromethane, chlorodifluoromethane (R-22), 1,2,2-trifluoro-1,1,2-trichloroethane, 1,1-dichloro-2,2,2-trifluoroethane (R-123), 1,1-dichloro-1-fluoroethane,-1-chloro-2,2,2-trifluoroethane,-1-chloro-1,2,2,2-tetrafluoroethane (R-124), 1-chloro-1,1,2,2-tetrafluoroethane, dichloromethane, difluoromethane (R-32), 1,1,2,2,2-pentafluoroethane (R-125), 1,1,2,2-tetrafluoroethane (R-134), 1,1,1,2-tetrafluoroethane (R-134a), 1,1,1-trifluoroethane (R-143a), 1,1-difluoroethane (R-152a), and mixtures thereof.

Among the refrigerant blends with which these oils can be advantageously used as lubricants are the binary mixtures of R-32 with R-125, R-152a, or R-134a; R-125/R-143a, R-290/R-134a, and R-22/R-152a binary blends; and ternary blends such as R-22/R-290/R-125, R-22/R-152a/R-124, R-32/R-125/R-'134a, and R-125/R-143a/R-134a.

The ability of the present invention to provide lubricants compatible with R-134a is perhaps its most valuable asset, since R-134a has been reported to have an ozone depletion potential of zero, therefore would be environmentally superior to the chlorofluorocarbon refrigerants most commonly used in refrigeration applications, but has the disadvantage of not being compatible with the lubricants normally used in those applications. However, as already mentioned, the ester oils have general utility as lubricants; and they have uses in other applications too. For example, (1) having relatively low volatilities at given viscosities, they can be utilized as hydraulic fluids in metal working, electrical generation, and mining industries, optionally in conjunction with soluble polymers, such as styrene-diene polymers, (2) having a relatively high smoke point for a given viscosity, they can be used in spin finish formulations in the textile industry and in other such applications where it is undesirable to release smoke into the working environment, and (3) those having the best thermal stabilities can also be employed in applications such as turbine oils, rolling oils, and compressor oils.

The ester oils are preferably prepared by (1) reacting a $Z'-CH(COOR)_2$ donor in which $Z'$ is most preferably hydrogen with a $CTT'=CT''COOR$ acceptor to form a $Z-C(COOR)_2-(CTT'-CT''COOR)_w-CT'-CHT''COOR$ product which is characterized by (a) being composed primarily of molecules wherein Z is most preferably $-(CTT'-CT''COOR)_r-CT'-CHT''COOR$, at least some of the Rs (which may be the same or different) are lower alkyls of 1–8 carbons, each of t and w is zero or a positive integer, and the sum of t and w is 0-28 and (b) having at least three acceptor moieties in at least about 25%, preferably at least about 40% of those molecules and (2) when desired (especially when all of the Rs are methyl) transesterifying the resultant intermediate product by reacting it with one or more alcohols containing more carbons per molecule than the lower alkyl groups of the intermediate.

In the practice of this preferred embodiment of the invention, the intermediate product may be recovered from its synthesis reaction mixture and, if desired, may also be fractionated into separate components before being subjected to transesterification. However, it is frequently preferable to transesterify the intermediate without first separating it from its synthesis reaction mixture.

Regardless of whether the transesterification is conducted on a recovered or unrecovered intermediate, it is accomplished by contacting the intermediate with one or more alcohols containing more carbons per molecule than the alkyl groups to be replaced and maintaining contact between the reactants at a suitable temperature until the desired transesterification has been effected. Alcohols most apt to be desirable for use in the reaction are substituted and unsubstituted alkanols, cycloalkanols, and aralkanols containing up to about 30 carbons (e.g., ethanol, chloroethanol, propanol, butanol, hexanol, bromohexanol, heptanol, octanol, decanol, fluorodecanol, dodecanol, hexadecanol, octadecanol, eicosanol, tetracosanol, triacontanol, cyclohexanol, cyclooctanol, benzyl alcohol, p-methylbenzyl alcohol, phenethyl alcohol, phenylpropanol, phenylpentanol, and phenethylbenzyl alcohol), as well as the aliphatic, cycloaliphatic, and araliphatic alcohols containing up to 30 carbons and also containing hetero atoms, such as oxygen, phosphorus, or sulfur (e.g., ethylthioethanol, ethoxyethanol, and the like).

The amount of alcohol employed in the transesterification reaction varies with the degree of transesterification desired, the quantity generally being the stoichiometric amount or an amount slightly in excess of the stoichiometric requirement. For example, when the intermediate contains an average of four ester groups per molecule, and it is wished to replace substantially all of those ester groups with the alcohol or alcohols used in the transesterification reaction, the amount of alcohol added to the intermediate should be at least four mols/mol of intermediate. Only about half as much alcohol would be added, on the other hand, when the objective is to replace approximately half of the ester groups of the intermediate.

Use of a transesterification reaction after completion of the Michael reaction permits a wide variety of products to be prepared from any particular product of the Michael reaction—final products having only the short ester chains which favor solubility in a refrigerant such as R-134a, final products having only the longer ester chains which increase viscosity, and final products having a controlled mix of short and longer ester chains to provide desired intermediate degrees of solubility and viscosity.

The transesterification is suitably conducted at an elevated temperature which provides for reflux and removal of a lower alcohol by-product from the reaction mixture without permitting undue loss of the higher alcohol reactant(s) from the reaction vessel, e.g., a temperature of about 50°-180° C. Although the reaction does not require catalysis, it is accelerated by the use of a base, which may be the base already present when the Michael reaction product is transesterified without first being recovered from its synthesis reaction mixture. It is sometimes desirable to add a catalytic amount of a base to accelerate the reaction, especially when the Michael product has been recovered before being subjected to transesterification. However, when such an addition is made, the amount of catalyst added is preferably kept low enough to prevent interference with the reaction or with subsequent separation of the products from the reaction mixture. Such an amount is typically about 0.05-1.0 g/kg of the Michael reaction product to be transesterified.

In another preferred embodiment of the invention, reaction products obtained from Michael donors and acceptors in which less than all of the electron withdrawing groups are ester groups (e.g., products obtained from methyl acetoacetate and methyl acrylate and products obtained from dimethyl malonate and methacrylonitrile) are subjected to a transesterification reaction to replace some or all of the ester groups with higher ester groups. Desirable ester products can also be obtained by subjecting a Michael reaction product containing nitrile groups to simultaneous hydrolysis and esterification with one or more alcohols in order to replace some or all of the nitrile groups with ester groups.

The products resulting from the Michael reaction or from conversion of the Michael reaction products to derivatives are typically washed with water to remove any unreacted materials and catalyst prior to being used in their intended application; and, if desired, they may then be further purified by subjecting them to fractional distillation. They may then be utilized alone or together with other materials serving similar functions and/or with additives serving other functions in their intended application, e.g., as plasticizers, solvents, lubricants, molding materials, or any of the other uses mentioned above.

Additives particularly apt to be used together with the products of the invention are (1) the antioxidants frequently used in organic compositions, (2) epoxy and other dehydrating agents sometimes used in refrigeration compositions, and (3) the oxidation resistance and thermal stability improvers, corrosion inhibitors, metal deactivators, lubricity additives, viscosity index improvers, pour and/or floc point depressants, detergents, dispersants, antifoaming agents, anti-wear agents, and extreme pressure resistance additives conventionally used in lubricant compositions. Also, when used as refrigeration lubricants, they are used in conjunction with refrigerants (such as those mentioned above), although they can be mixed with the refrigerants in situ rather than being combined with them prior to use.

The following examples are given to illustrate the invention and are not intended as a limitation thereof.

EXAMPLE 1

Charge a suitable reaction vessel with 792 g (6 mols) of dimethyl malonate, 52.8 g (0.4 mol) of potassium carbonate, 12 g (0.035 mol) of tetrabutylammonium hydrogen sulfate, and 1290 g (15 mols) of methyl acrylate. After stirring the reaction mixture at room temperature for ~18 hours, slowly heat it to ~50° C. to effect a rapid rise of the temperature of the reaction mixture to reflux. Maintain the reaction mixture at reflux for ~15 minutes and then cool to room temperature over a period of ~1 hour. A heavy solid mass forms in the bottom of the reaction vessel during cooling. Dilute this mass with methylene chloride, wash with five 1.5-L portions of water, and subject the product to gas chromatographic (GC) analysis. The analysis shows the product to consist, in area percentages, of 4.3% trimethyl ester of 1,1,3-propanetricarboxylic acid, 70% tetramethyl ester of 1,3,3,5-pentanetetracarboxylic acid, 18% pentamethyl ester of 1,3,3,5,7-heptanepentacarboxylic acid, and 7.7% polyesters, i.e., products having more than five ester groups per molecule.

EXAMPLE 2

Conduct two additional Michael reactions between dimethyl malonate and methyl acrylate using tetrabutylammonium hydrogen sulfate as the phase transfer catalyst as in Example 1 but employing sodium methoxide as the base, 80 ° C. as the reaction temperature, and methyl acrylate/dimethyl malonate tool ratios of 8/1 (reaction mixture 2-A) and 10/1 (reaction mixture 2-B) respectively. Monitor the reactions by GC and discontinue them when the following analyses are obtained:

Reaction mixture 2-A: 32% tetramethyl ester of 1,3,3,5-pentanetetracarboxylic acid, 24% pentamethyl ester of 1,3,3,5,7-heptanepentacarboxylic acid, 11% hexamethyl ester of 1,3,5,5,7,9-nonanehexacarboxylic acid, 8% heptamethyl ester of 1,3,5,5,7,9,11-undecaneheptacarboxylic acid, 2% octamethyl ester of 1,3,5,7,7,9,11,13-tridecaneoctacarboxylic acid, and smaller amounts of higher esters Reaction mixture 2-B: 20% tetramethyl ester, 22% pentamethyl ester, 19% hexamethyl ester, 14% heptamethyl ester, 9% octamethyl ester, and smaller amounts of higher esters Then work up the product mixtures by diluting them with solvent, washing to neutrality with water, and removing solvent, water, and lower boiling products by distillation to form viscous oils which, in each case, are completely miscible with R-134a over a temperature range of −40° C. to 70° C.

EXAMPLE 3

Charge a suitable reaction vessel with 660 g (5 mols) of dimethyl malonate, 35 g (0.25 mol) of potassium carbonate, and 1.75 g (0.005 mol) of tetrabutylammonium hydrogen sulfate. Heat the stirred mixture to 120° C., and add 2048 g (16 mols) of n-butyl acrylate over a period of six hours while monitoring the reaction by GC, which shows the dibutyl dimethyl ester of 1,3,3,5-pentanetetracarboxylic acid to be the major product at the end of this period. Then heat the reaction mixture at 150° C. for three hours to form a product mixture containing the tributyl dimethyl ester of 1,3,3,5,7-heptanepentacarboxylic acid. Cool the resulting reaction mixture to room temperature, add water and toluene, wash repeatedly with water until neutral, remove the water and toluene by azeotropic distillation, and then remove light products at 180°-185° C. and 0.1-0.15 mmHg to provide a heavy oil having a viscosity of 96 mm$^2$.s$^{-1}$ at 40° C., a viscosity of 11.6 mm$^2$.s$^{-1}$ at 100° C., a viscosity index of 109, and excellent miscibility with R-134a over a temperature range of −60° C. to 80° C.

EXAMPLE 4

Using a dimethyl malonate/methyl acrylate Michael reaction and workup procedure similar to that of the preceding examples, prepare a 20.8 g sample of a mixture of 66% tetramethyl ester of 1,3,3,5-pentanetetracarboxylic acid, 26% pentamethyl ester of 1,3,3,5,7-heptanepentacarboxylic acid, and 6% hexamethyl and heptamethyl esters. Treat the mixture with 0.1 mol of butanol and 0.1 mol of hexanol at 120° C. in the presence of a catalytic amount of 10% sodium methoxide, remove the volatiles by distillation, and work up to provide an oil which has a viscosity of 159 mm$^2$.s$^{-1}$ at 40° C., a viscosity of 14.6 mm$^2$.s$^{-1}$ at 100° C., a viscosity index of 88, and total miscibility with R-134a.

EXAMPLE 5

Charge a reaction vessel with 15.8 Kg (120 mols) of dimethyl malonate, 158 g (1.2 mols) of potassium carbonate, and 37 g (0.1 mol) of tetrabutylammonium hydrogen sulfate under nitrogen. Heat the reactor to ~70° C., add 25.8 Kg (300 mols) of methyl acrylate over six hours, and then heat the reaction mixture at 70°-80° C. for at least 10 hours to form a product mixture containing a major amount of tetramethyl ester of 1,3,3,5-pentanetetracarboxylic acid, smaller amounts of pentamethyl and higher esters, and a minor amount of trimethyl ester of 1,1,3-propanetricarboxylic acid.

Charge 22 Kg (296 mols) of n-butanol and 30.3 Kg (296 mols) of n-hexanol to the reactor and heat at 110°-120° C. while collecting the volatiles overhead. After removing the stoichiometric amount of methanol, cool the reaction mixture to room temperature, dilute with toluene, wash to neutrality with water, dry by the azeotropic removal of water, and heat treat the crude under reduced pressure.

Distillation under reduced pressure (1 mmHg) and 200°-250° C. provides an oil which has a viscosity of 17 mm$^2$.s$^{-1}$ at 40° C., a viscosity of 3.6 mm$^2$.s$^{-1}$ at 100 ° C., a total acid number (TAN) of 0.025 mgKOH/g, a water content of 64 ppm, and total miscibility with R-134a over a temperature range of −60° C. to 80° C. The bottoms product is an oil having a viscosity of 24.8 mm$^2$.s$^{-1}$ at 40° C., a viscosity of 4.7 mm$^2$.s$^{-1}$ at 100° C., a total acid number of 0.034 mgKOH/g, a water content of 73 ppm, and total miscibility with R-134a over a temperature range of −60° C. to 80° C.

EXAMPLE 6

Charge a reaction vessel with 3.3 g (0.05 mol) of malononitrile, 0.7 g (0.005 mol) of potassium carbonate, and 0.17 g (0.5 mmol) of tetrabutylammonium hydrogen sulfate under nitrogen. Slowly add 11.2 g (0.2 mol) of acrylonitrile at 50° C. with stirring and maintain the temperature at 50°-70 ° C. for 3 hours. Then cool the reaction mixture to room temperature, dissolve in ethyl acetate, wash with water until neutral, dry over magnesium sulfate, filter, and concentrate to provide a solid mass which spectroscopic analysis indicates to contain more than two acrylonitrile moieties per molecule.

EXAMPLE 7

Charge a reaction vessel with 3.3 g (0.05 mol) of malononitrile, 0.7 g (0.005 mol) of potassium carbonate, and 0.17 g (0.5 mmol) of tetrabutylammonium hydrogen sulfate. Heat the mixture to 50° C. under nitrogen and slowly add 10.8 g (0.125 mol) of methyl acrylate at a rate such as to maintain the temperature under 80 ° C. Keep the reaction mixture at 70–80° C. for two hours, cool to room temperature, dilute with dichloromethane, wash with water until neutral, dry over magnesium sulfate, filter, and concentrate to provide a solid mass which spectroscopic analysis shows to contain dimethyl ester of 3,3-dicyano-1,5-pentanedicarboxylic acid, trimethyl ester of 5,5-dicyano-1,3,7-heptanetricarboxylic acid, and smaller amounts of higher molecular weight components.

What is claimed is:

1. A process which comprises reacting at least one Michael donor corresponding to the formula $Z'$—CH(E)(E'')$ in which $Z'$ is hydrogen, alkyl, or cycloalkyl and $E''$ is hydrogen or an electron withdrawing group selected from the group consisting of —CN, —COOR, —C(O)R', —OAr, —OR, —NR$_2$, —SO$_2$R, —SO$_2$AR, —S(O)R', —SR, —CF$_3$, —F, —Cl, —BR, and —I, in which Ar is an aryl group and R and R' are aliphatic, cycloaliphatic, or alphyl groups of up to 30 carbons, with the proviso that R' may represent hydrogen with at least one Michael acceptor corresponding to the formula $CTT'$=$CT''G$ in the presence of a basic compound and a phase transfer catalyst until at least 25% of the product molecules correspond to the formula $Z$—$C(E)(E')_p$—$Q_s$ in which Z is alkyl, cycloalkyl, or —$(CTT'$—$CT''G)_w$—$CTT$—$CHT''G$; Q is —$(CTT'$—$CT''G)_t$—$CTT$—$CHT''G$; p is zero or one; s is respectively two or one; and each of t and w represents zero or a positive integer such that the molecule contains at least three acceptor moieties -T, T' and T'' in the above formulas being independently selected from the group consisting of hydrogen, G' and the groups alkyl alkoxyalkyl, alkylthioalkyl, cycloalkyl, dialkylaminocycloalkyl, aryl, haloaryl, alkoxyaryl, aralkyl and alkaryl, said groups having up to 20 carbon atoms; and E, E', G and G' are independently selected from the groups consisting of —CN, —COOR, —C(O)R', —OAr, —OR, —NR$_2$, —SO$_2$R, —SO$_2$Ar, —S(O)R', —SR, CF$_3$, —F, Cl, —Br, and —I, in which Ar is an aryl group and R and R' are aliphatic, cycloaliphatic, or alphyl groups of up to 30 carbons, with the proviso that R' may represent hydrogen.

2. The process of claim 1 wherein the reaction between the Michael donor and Michael acceptor is continued until at least 25% of the product molecules contain 3–30 acceptor moieties/molecule.

3. The process of claim 2 wherein at least one of the E and G groups is —COOR.

4. The process of claim 3 wherein $Z'$ is hydrogen, E and $E''$ are —COOR groups, $CTT'$=$CT''G$ is $CH_2$=$CHCOOR$, and at least 25% of the product molecules correspond to the formula $ROOCCH_2CH_2$—$(ROOCCHCH_2)_w$—$C(COOR)_2$—$(CH_2CHCOOR)_t$—$CH_2CH_2COOR$ in which the sum of t and w is 1–28 and the —COOR groups are independently selected from —COOR groups in which R is an alkyl of 1–8 carbons.

5. The process of claim 4 wherein the product of the reaction between the Michael donor and Michael acceptor is reacted with one or more alcohols containing more carbons than at least some alkyls of the Michael reaction product to replace at least some of those alkyls with higher hydrocarbyl groups containing up to 30 carbons.

* * * * *